United States Patent
Kohn et al.

(10) Patent No.: US 7,271,234 B2
(45) Date of Patent: Sep. 18, 2007

(54) POLYARYLATES FOR DRUG DELIVERY AND TISSUE ENGINEERING

(75) Inventors: Joachim B. Kohn, Plainfield, NJ (US); Satish Pulapura, Bridgewater, NJ (US); Arthur Schwartz, Windsor, NJ (US); Raman Bahulekar, Edison, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 10/512,609

(22) PCT Filed: Apr. 24, 2003

(86) PCT No.: PCT/US03/12883

§ 371 (c)(1),
(2), (4) Date: Oct. 25, 2004

(87) PCT Pub. No.: WO03/091337

PCT Pub. Date: Nov. 6, 2003

(65) Prior Publication Data

US 2005/0165203 A1 Jul. 28, 2005

Related U.S. Application Data

(60) Provisional application No. 60/375,846, filed on Apr. 24, 2002.

(51) Int. Cl.
*C08G 64/00* (2006.01)

(52) U.S. Cl. .................. 528/196; 264/176.1; 264/219; 428/411.1; 528/176; 528/182; 528/198; 528/206; 506/40

(58) Field of Classification Search ............. 264/176.1, 264/219; 428/411.1; 528/176, 182, 196, 528/198, 206; 506/40
See application file for complete search history.

(56) References Cited

U.S. PATENT DOCUMENTS

| 5,216,115 A | * | 6/1993 | Kohn et al. ................. 528/176 |
| 5,587,507 A | | 12/1996 | Kohn et al. ................... 560/40 |
| 5,670,602 A | | 9/1997 | Kohn et al. ................. 528/176 |
| 6,120,491 A | | 9/2000 | Kohn et al. ................. 604/502 |
| 2004/0254334 A1 | * | 12/2004 | James et al. ................. 528/310 |

OTHER PUBLICATIONS

A Combinatorial Approach for Polymer Design, American Chemical Society, 119, (19) 4553-4554, 1997.*
Brocchini et al.; A Combinatorial Apprach for Polymer Design; Feb. 5, 1997; J.Am. Chem. Society 1997,119,4553-4554.

* cited by examiner

*Primary Examiner*—Terressa Boykin
(74) *Attorney, Agent, or Firm*—Synnestvedt Lechner & Woodbridge LLP

(57) ABSTRACT

Biocompatible polyarylates of tyrosine-derived diphenol compounds and poly(alkylene oxide) dicarboxylic acids, articles formed therefrom and therapeutic uses are disclosed.

43 Claims, 5 Drawing Sheets

POLYARYLATES FOR DRUG DELIVERY AND TISSUE ENGINEERING

CROSS REFERENCE TO RELATED APPLICATIONS

This application claims the priority of PCT Application No. PCT/US03/12883 filed on Apr. 24, 2003, and U.S. Provisional Application No. US 60/375,846 filed on Apr. 24, 2002, the contents of which are hereby incorporated by reference.

FIELD OF THE INVENTION

The present invention relates to bioerodable polyarylates co-polymers of tyrosine-derived dipeptides and functionalized poly(alkylene oxides). The present invention further relates to injectable composition and implantable articles for drug delivery and tissue engineering made from these polymers.

BACKGROUND

The biotechnology industry has evolved to allow the large scale production of recombinant proteins for commercial use. However, many of these therapeutic proteins and vaccines present a unique challenge for drug delivery. The successful clinical application or commercial use of many proteins requires the use of a protein delivery system to reduce the frequency of administration, provide a lower toxicity through a reduced peak serum concentration, localize the drug at the site of action, or yield a steady-state level of the drug to achieve the desired effect. The biggest challenge however is to maintain the stability of proteins during the formulation steps.

Proteins are generally not very stable, as the stabilization energy of the native state is mostly between 5 and 20 kcal/mol, which is equivalent to that of a few hydrogen bonds. Many forces are involved in keeping the native proteins properly folded including hydrophobic interactions, electrostatic interactions (charge repulsion and ion pairing), hydrogen bonding, intrinsic propensities, and van der Waals forces. Among these forces, hydrophobic interactions seem to be the dominant.

There are many factors that affect protein stability. These include at least temperature, pH, ionic strength, metal ions, surface adsorption, shearing, shaking, additives, solvents, protein concentration, purity, morphism, pressure, freeze-thawing and drying. Most mesophilic proteins, such as those from human beings, can be denatured easily at temperatures between 50 to 80° C. A common phenomenon of protein instability is the formation of protein aggregates, which can be soluble or insoluble, chemical or physical, and reversible or irreversible. Chemical transformations that lead to protein instability include at least deamidation, oxidation, hydrolysis, isomerization, succinimidation, disulfide bond formation and breakage, non-disulfide cross linking and deglycosilation. It is therefore clear that developing a delivery system for proteins is not a trivial matter.

The most common approach used to develop a controlled delivery system for proteins is to encapsulate the protein in a polymer matrix or microsphere of poly(lactic-co-glycolic acid) (PLGA), which has been used for over twenty years as a resorbable suture material. A great deal of research has been published on the development of protein-controlled release formulations using PLGA microspheres. However, there are only a small number of successful commercial formulations using this system. A biodegradable microsphere formulation, the Lupron Depot, has been commercially successful for several years. This formulation consists of leuprolide acetate, a decapeptide, encapsulated in biodegradable microspheres of PLGA for the treatment of prostate cancer, endometriosis, and precocious puberty. The drug is released continuously over either one or three months depending upon the formulation. A biodegradable human growth hormone microsphere formulation is presently marketed by Alkermes, Inc.

PLGA microspheres are usually prepared by a solvent-based process, which as discussed above, is harmful to protein stability and activity. Melt processing is not a viable alternative, because the $T_g$ of the PLGA system is in the range of 55 to 60° C. Thus, melt processing has to be conducted at relatively high temperatures that are detrimental to the stability and activity of the proteins. PLGA degradation also releases acidic byproducts, which can inactivate the proteins.

Drug delivery systems require a product that is injectable through a 21 gauge needle and from which a protein can be delivered at a sustained rate for two to four weeks without loss of activity. Water may be used as a diluent to allow injection through a narrow bore needle, and stabilizers such as sugars or salts may be used.

Accordingly, there exists a need for a biocompatible low viscosity polymer that is degradable and resorbable and able to absorb water or be emulsified in water so that water can be used as a diluent, if necessary. Ideally, for drug delivery purposes, the polymer should be fluid at room temperature. However, polymers that become fluid with heating to temperature below the temperature at which proteins denature are also suitable.

SUMMARY OF THE INVENTION

This need is met by the present invention. It has now been discovered that tyrosine-derived diphenols can be copolymerized with poly(alkylene oxide) dicarboxylic acids to form non-toxic bioerodable polyarylates meeting the above drug delivery system requirements. Higher molecular weight and viscosity versions of these polymers also possess desirable tissue engineering properties.

Therefore, according to one aspect of the present invention, polyarylates are provided that have repeating structural units according to Formula I

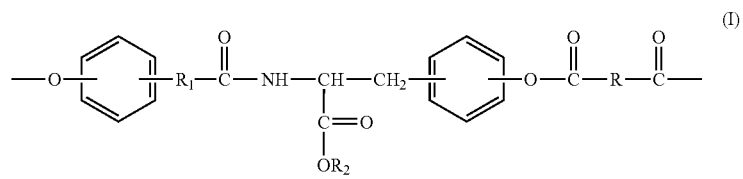

wherein $R_1$ is CH=CH or $(CH_2)_n$ wherein n is from 0 to 18, inclusive; $R_2$ is selected from hydrogen and straight and branched alkyl and alkylaryl groups containing up to 18 carbon atoms; and R has the structure of Formula IIa or IIb:

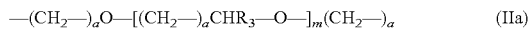
(IIa)

and

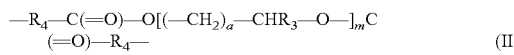
(IIb)

wherein a is from 1 to 3, inclusive, m is from 1 to 500,000, inclusive, $R_3$ is hydrogen or a lower alkyl group containing from one to four carbon atoms, and $R_4$ is selected from a bond or straight and branched alkyl and alkylaryl groups containing up to 18 carbon atoms.

The pendant side chains on each polyarylate repeating unit provide a further degree of freedom in the design of the polyarylates and can be used to modify the overall physicomechanical properties of the polymer without changing the polymer backbone structure. This allows for the systemic variation in polymer structure, which leads to the development of structure-property relationships. The polyarylates of the present invention are expected to exhibit orthogonal relationships, which allows the variation of many properties independent of others.

The polymers of the present invention have low melting/softening points, which will facilitate their formulation with temperature sensitive biologically or pharmaceutically active compounds such as proteins by permitting the active compounds and polymers to be directly mixed without solvents or heating. Therefore, according to another embodiment of the present invention, the polymers are combined with a quantity of biologically or pharmaceutically active compound sufficient for effective site-specific or systemic drug delivery as described by Gutowska, et al., *J. Biomater. Res.*, 29, 811-21 (1995), and Hoffman, *J. Controlled Release*, 6, 297-305 (1987). The biologically or pharmaceutically active compound may be physically admixed, embedded in or dispersed in the polymer matrix.

Accordingly, in yet another aspect of the present invention, a method is provided for site-specific or systemic drug delivery by administering to a patient in need thereof a therapeutically effective amount of a biologically or pharmaceutically active compound in combination with the polymer of the present invention. The polymer drug combinations of the present invention include combinations in which the polymer functions as a degradable matrix for the suspension of drug loaded microparticles to control the rate of release and to prevent microparticle migration.

Implantable medical materials and devices formed from the polymers of the present invention are also included in the scope of the present invention. In accordance with this aspect of the present invention, the polymers of the present invention may be used as binding agents for making shapable putties from solid materials such as hydroxyapatite, calcium sulfate, tricalcium phosphate, demineralized bone matrix, bioglass, and the like, or used alone as a temporary filling material in cosmetic reconstructive surgery.

The poly(alkylene oxide)monomeric repeating units decrease the surface adhesion of the polymers of the present invention. As the value of m in Formulae IIa and IIb increases, the surface adhesion decreases. Polymer coatings may thus be prepared that are resistant to cell attachment and useful as non-thrombogenic coatings on surfaces in contact with blood. Such polymers also resist bacterial adhesion in this, and in other medical applications as well. The present application therefore includes blood contacting devices and medical implants having surfaces coated with the polymers of the present invention. The surfaces are preferably polymeric surfaces. The methods according to the present invention include implanting in the body of a patient a blood-contacting device or medical implant having a surface coated with the polymers of the present invention.

The polymers of the present invention have good film-forming properties. An important phenomenon observed is the temperature-dependent inverse phase transition of the polymers in aqueous solution. As temperature increases, the polymers undergo an inverse phase transition to a collapsed state. Stated another way, the polymers form gels upon heating. Therefore, the present invention also includes aqueous polymer compositions that gel upon heating. Polymers that undergo the inverse phase transition at about 30 to 40° C. on heating can be used as biomaterials for drug release and clinical implantation materials. Specific applications include films and sheets for the prevention of adhesion and for tissue reconstruction.

Therefore, in another embodiment of the present invention, the polymers of the present invention may be formed into a sheet or a coating for application to exposed injured tissues for use as a barrier for the prevention of surgical adhesions as described by Urry, et al., *Mat. Res. Soc. Symp. Proc.*, 292, 253-264 (1993). Therefore, another aspect of the present invention provides a method for preventing the formation of adhesion between injured tissues by inserting as a barrier between the injured tissues a sheet or coating of the polymers of the present invention.

A more complete appreciation of the invention and many other intended advantages can be readily obtained by reference to the following Detailed Description of the Preferred Embodiment and claims, which disclose the principles of the invention and the best modes which are presently contemplated for carrying them out.

DETAILED DESCRIPTION OF THE PREFERRED EMBODIMENTS

Figure 1:
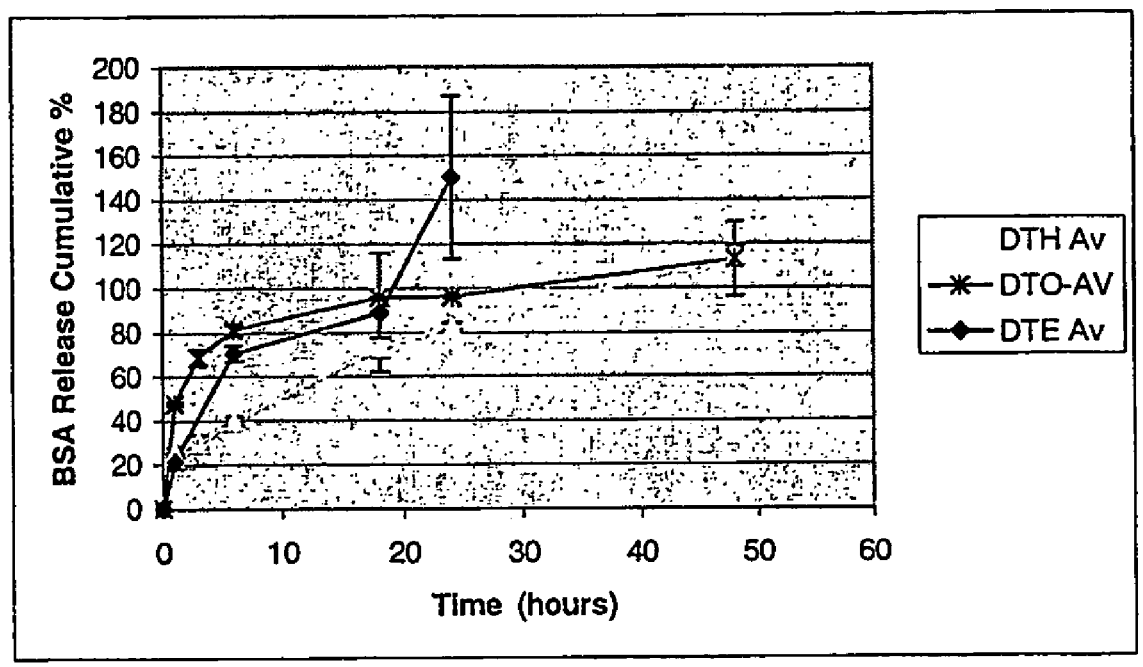
FIG. 1 depicts the release of BSA from DTR-PEG 600.

The polyarylates of the present invention are prepared by the condensation of a diacid with a diphenol according to the method described by U.S. Pat. No. 5,216,115 in which diphenol compounds are reacted with aliphatic or aromatic dicarboxylic acids in a carbodiimide mediated direct polyesterification using 4-(dimethylamino)-pyridinium-p-toluene sulfonate (DPTS) as a catalyst. The disclosure of U.S. Pat. No. 5,216,115 in this regard is incorporated herein by reference.

The diphenol compounds are the tyrosine-derived diphenol monomers of U.S. Pat. Nos. 5,587,507 and 5,670,602, the disclosures of both of which are also incorporated herein by reference. The polyarylates of Formula I are prepared using tyrosine-derived diphenol monomers having the structure of Formula III:

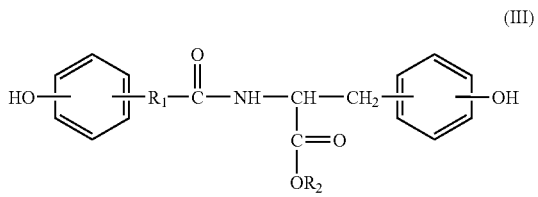

(III)

wherein $R_1$, $R_2$ and n are the same as described above with respect to Formula I.

The preferred diphenol monomers are desaminotyrosyl-tyrosine carboxylic acids and esters thereof, wherein $R_1$ is —$CH_2$—$CH_2$—, which are referred to as DT esters. For purposes of the present invention, the ethyl ester ($R_2$=ethyl) is referred to as DTE, the benzyl ester ($R_2$=benzyl) as DTBn, and so forth. Both patents disclose methods by which these monomers may be prepared. For purposes of the present invention, the desaminotyrosyl-tyrosine free carboxylic acid ($R_2$=hydrogen) is referred to as DT.

It is not possible to polymerize the polyarylates having pendant free carboxylic acid groups from corresponding diphenols with pendant free carboxylic acid groups without cross-reaction of the free carboxylic acid groups with the co-monomer. Accordingly, polyarylates that are homopolymers or copolymers of benzyl ester diphenyl monomers such as DTBn may be converted to corresponding free carboxylic acid homopolymers and copolymers through the selective removal of the benzyl groups by the palladium catalyzed hydrogenolysis method disclosed by co-pending and commonly owned U.S. Pat. No. 6,120,491. The disclosure of this patent is incorporated by reference. The catalytic hydrogenolysis is necessary because the lability of the polymer backbone prevents the employment of harsher hydrolysis techniques.

The dicarboxylic acids are derived from poly(alkylene oxides) such as polyethylene glycol, polypropylene glycol, polybutylene glycol, Pluronics and the like. Polyethylene glycol diacids are preferred.

Two classes of diacids are disclosed. The first class produces polymers in which R has a structure according to Formula IIa. These diacids have the structure of Formula IVa:

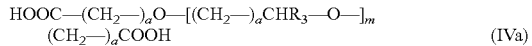

(IVa)

wherein a, m and $R_3$ are the same as described above with respect to Formula IIa. $R_3$ is preferably hydrogen, a is preferably 1, and m is preferably between about 10 and about 100, and more preferably between about 10 and about 50.

The diacids of Formula IVa are formed by the oxidation of poly(alkylene oxides) according to well-known methods. One example of such a compound is biscarboxymethyl polyethylene glycol, which is commercially available.

The second class of diacids produces polymers in which R has a structure according to Formula IIb. These diacids have the structure of Formula IVb:

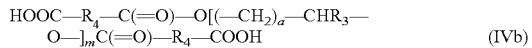

(IVb)

wherein a, m and $R_3$ are again the same as described above with respect to Formulae IIa or IIb. Again, $R_3$ is preferably hydrogen, a is preferably 1, and m is preferably between about 10 and about 100, and more preferably between about 10 and about 50. $R_4$ is the same as described above with respect to Formula IIb.

The dicarboxylic acids of Formula IVb are poly(alkylene oxides)bis-functionalized with dicarboxylic acids having the structure of Formula V:

(V)

wherein $R_4$ is the same as described above with respect to Formula IIB, and preferably contains up to 12 carbon atoms.

The poly(alkylene oxides) of Formula IVb that are bis-functionalized with dicarboxylic acid are prepared by the reaction of a non-functionalized poly(alkylene oxide) with an excess of either the dicarboxylic acid (mediated by a coupling agent such as dicyclohexyl carbodiimide), the anhydride (e.g. succinic anhydride) in the presence of pyridine or triethylamine, or a dicarboxylic acid chloride (e.g. adipoyl chloride) in the presence of an acid acceptor like triethylamine.

For the dicarboxylic acids of Formula IVa, $R_4$ is preferably selected so that the dicarboxylic acids employed as starting materials to bis-functionalize the poly(alkylene oxides) are either important naturally-occurring metabolites or highly biocompatible compounds. Preferred Formula V dicarboxylic acid starting materials therefore include the intermediate dicarboxylic acids of the cellular respiration pathway known as the Krebs cycle. These dicarboxylic acids include alpha-ketoglutaric acid, succinic acid, fumeric acid, malic acid and oxaloacetic acid, for which $R_4$ is —$CH_2$—$CH_2$—C(=O)—, —$CH_2$—$CH_2$—, —CH=CH=, —$CH_2$—CH(—OH)— and —$CH_2$—C(=O)—, respectively.

Another naturally-occurring, preferred dicarboxylic acid starting material is adipic acid ($R_4$=(—$CH_2$—)$_4$), found in beet juice. Other preferred biocompatible dicarboxylic acids include oxalic acid (no $R_4$), malonic acid ($R_4$=—$CH_2$—), glutaric acid ($R_4$=($CH_2$—)$_3$, pimellic acid ($R_4$=(—$CH_2$—)$_5$, suberic acid ($R_4$=(—$CH_2$—)$_6$ and azalaic acid ($R_4$=(—$CH_2$—)$_7$. In other words, among the dicarboxylic acids suitable for use in the present invention are compounds in which $R_4$ represents (—$CH_2$—)$_z$ wherein z is an integer between 0 and 12, inclusive. A preferred class of highly biocompatible aromatic dicarboxylic acids are the bis(p-carboxyphenoxy) alkanes such as bis(p-carboxyphenoxy)propane.

The polyarylates of the present invention degrade by hydrolysis into the original starting materials, i.e., the tyrosine-derived diphenols and the poly(alkylene oxide) dicarboxylic acids. The poly(alkylene oxide) dicarboxylic acids that are poly(alkylene oxides)bis-functionalized with dicarboxylic acids further degrade to the starting poly(alkylene oxides) and dicarboxylic acids.

The polyarylates of the present invention are highly hydrophilic, which is advantageous for polymeric drug delivery systems. However, the hydrophilic:hydrophobic balance of the polyarylates can be varied in several ways. The ester of the pendant chain of the diphenol can be changed, with longer-chain ester groups increasing hydrophobicity. Increasing the molecular weight of the poly(alkylene oxide) or increasing the number of carbons in the alkylene group of the poly(alkylene oxide) will also increase hydrophobicity. Changing the dicarboxylic acid used to bis-functionalized the poly(alkylene oxide) will also change the hydrophilic:hydrophobic balance.

Preferred polyarylates have weight average molecular weights between about 1,000 and 500,000 daltons, preferably between about 3,000 and 50,000 daltons, and more preferably between about 5,000 and 15,000 daltons. Molecular weights are calculated by gel permeation chromatography relative to polystyrene standards in tetrahydrofuran without further correction.

The molecular weights of the polyarylates can be controlled either by limiting the reaction time or the ratios of either component. Molecular weights can also be controlled by the quantity of the carbodiimide coupling reagent that is used. The viscosities of the polyarylates of the present invention can also be reduced by mixing with water to form either an aqueous solution or emulsion of the polymer.

Iodine- and bromine-containing polymers are radio-opaque. These polymers and their methods of preparation are disclosed by U.S. Pat. No. 6,475,577. The disclosure of this patent is incorporated herein by reference. Radio-opaque polymers include repeating structural units in which one or more hydrogens of an aromatic ring, an alkylene carbon, or both, are replaced with an iodine or bromine atom. The polyarylates of the present invention may be similarly iodine- and bromine-substituted. Polyarylates according to the present invention comprising the repeating structural units of Formula I are radio-opaque when copolymerized with radio-opaque monomers so that the polyarylates also contain radio-opaque repeating structural units, preferably one or more of the repeating structural units of Formula I in which one or more hydrogens of an aromatic ring, an alkylene carbon, or both, have been replaced with an iodine or bromine atom.

Cellular attachment, migration and proliferation on the surface of the polyarylates can be modulated as a function of poly(alkylene oxide) content, with attachment, migration and proliferation decreasing as poly(alkylene oxide) content increases. The present invention therefore includes methods for regulating cellular, attachment, proliferation and migration on the surface of a polymeric substrate by contacting living cells, tissues or biological fluids containing living cells with the polyarylates of the present invention. The polyarylates of the present invention are therefore particularly well-suited for use as coatings on medical implants, barriers for preventing the formation of adhesions between injured tissues, and polymer scaffolds for tissue engineering.

The polyarylates of the present invention may be formed into porous polymer scaffolds for tissue engineering by the methods disclosed by U.S. Pat. No. 6,103,255. The disclosure of this patent is also incorporated herein by reference. Porous polymer scaffolds prepared from the inventive polyarylates may incorporate an effective amount of the biologically active substance that either promotes or prevents a particular variety of cellular or tissue ingrowth. Examples of such substances include cell attachment mediators (such as the peptide containing variations of the "RGD" integrilin binding sequence known to affect cellular attachment), biologically active ligands, and substances that enhance or exclude particular varieties of cellular or tissue ingrowth. Such substances include, for example, osteoinductive substances (such as bone morphogenic proteins (BMP)), epidermal growth factor (EGF), fibroblast growth factor (FGF), platelet-derived growth factor (PDGF), insulin-like growth factor (IGF-I and II), TGFβ, and the like.

Any type of cell can be added to this scaffold for culturing and possible implantation, including cells of the muscular and skeletal system (such as condrocytes, fibroblasts, muscle cells and osteocytes), parenchymal cells such as hepatocytes, pancreatic cells (including Islet cells), cells of intestinal origin, and other cells such as nerve cells and skin cells, either as obtained from donors, from established cell culture lines, from embryonic and non-embryonic stem cells (human and non-human), or even before or after genetic engineering.

The polyarylates can be worked up by known methods commonly known in the field of synthetic polymers to produce a variety of useful articles with valuable physical and chemical properties, all derived from tissue compatible monomers. The useful articles can be shaped by conventional polymer-forming techniques. Molded articles prepared from the polyarylates are useful as degradable biomaterials for medical implant application. Molded articles may be prepared from the polyarylates, or the polyarylates may be coated on the surface of molded articles. Polymer coatings are particularly useful, because as poly(alkylene oxide) content increases, protein deposition and tissue adhesion decreases. Whether a portion of or the entire article, the polyarylates decompose harmlessly within a known period of time.

The polyarylates can also be formed into drug delivery systems that degrade to release pharmacologically or biologically active agents within a predictable controlled release time. The polyarylates of the present invention having low molecular weights, and consequently low viscosities and melting/softening points (including polymers that are liquid at temperatures below protein denaturation temperatures and as low as room temperature) are particularly well suited as carriers for injectable delivery systems for pharmacologically active biomolecules such as proteins, peptides, vaccines and genes, and the like, as well as other small pharmacologically active molecules. The low viscosities and melting/softening points permit the direct mixing of the active molecule and the polymer. The polyarylate release rate is determined by the hydrophilic:hydrophobic balance of the polymer. The more hydrophilic polymer, the faster the rate of release. Polymer degradation rate will also increase as hydrophilicity increases.

The low viscosity and softening/molecular weight polyarylates are also useful in the preparation of biodegradable liposomes and surfactants, and can be used as binding agents for making shapable putties from solids like hydroxyapatite, demineralized bone matrix and bioglass. These polyarylates can also be used in the preparation of degradable matrices for the suspension of drug loaded microparticle to control the rate of release and to prevent microsphere migration. Polyarylates that are solid at body temperature can also be used as temporary filling materials in cosmetic reconstructive surgery. Certain of the polyarylates that undergo inverse phase transitions upon heating may be applied as a room temperature liquid that then solidifies upon heating to body temperature.

The polyarylates of the present invention make possible the development of drug delivery systems having a number of advantages over the systems that are currently available or are being developed. Because the polyarylates are low viscosity materials, biologically and pharmaceutically active agents can be mixed in at room temperature without the addition of heat or organic solvents, representing a significant advance in the ease of product formulation. The present invention therefore also includes injectable delivery systems for biologically and pharmaceutically active compounds formed by directly mixing the active compound and polymer. The delivery system and its method of preparation are particularly well suited for use with active compounds such as pharmacologically active proteins, peptides, vaccines and genes, and the like, as well as other small pharmacologically active molecules, wherein the resulting mixtures can be injected without the use of excipients.

However, the mixtures form stable combinations with excipients, should the use of an excipient be desired. Both co-monomers, i.e., the tyrosine-derived diphenol and the poly(alkylene oxide) function to stabilize peptides and proteins. Release rates are easily controlled by adjustment of the hydrophilic:hydrophobic balance. Hydrophilic protein stabilizers, such as trehalose, may be optionally added. Finally, because the polyarylates degrade rapidly, this allows multiple sequential injections, if necessary. Degradation rates are controlled by altering the hydrophilic:hydrophobic balance.

The drug delivery systems of the present invention are suitable for applications where localized drug delivery is desired, as well as in situations where systemic delivery is desired. Therapeutically effective dosages may be determined by either in vivo or in vitro methods. For each particular compound of the present invention, individual determinations may be made to determine the optimal dosage required. The range of therapeutically effective dosages will naturally be influenced by the route of administration, the therapeutic objectives, and the condition of the patient. For the various suitable routes of administration, the absorption efficiency must be individually determined for each drug by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved. The release rate of the drug from the formulations of this invention are also varied within the routine skill in the art to determine an advantageous profile, depending on the therapeutic conditions to be treated.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of this invention may be administered several times daily, and other dosage regimens may also be useful.

The compositions may be administered subcutaneously, intramuscularly, colonically, rectally, nasally, orally or intraperitoneally, employing a variety of dosage forms such as suppositories, implanted pellets or small cylinders, aerosols, oral dosage formulations and topical formulations, such as ointments, drops and transdermal patches.

Acceptable pharmaceutical carriers for therapeutic use are well known in the pharmaceutical field, and are described, for example, in *Remington's Pharmaceutical Science*, Mac Publishing Co., (A. R. Gennaro edt. 1985). Such materials are non-toxic to recipients at the dosages and concentrations employed, and include diluents, solubilizers, lubricants, suspending agents, encapsulating materials, solvents, thickeners, dispersants, buffers such as phosphate, citrate, acetate and other organic acid salts, anti-oxidants such as ascorbic acid, preservatives, low molecular weight (less than about 10 residues) peptides such as polyarginine, proteins such as serum albumin, gelatin or immunoglobulins, hydrophilic polymers such as poly(vinylpyrrolindinone), amino acids such as glycine, glutamic acid, aspartic acid or arginine, monosaccharides, disaccharides, and other carbohydrates including cellulose or its derivatives, glucose, mannose or dextrines, chelating agents such as EDTA, sugar alcohols such as mannitol or sorbitol, counter-ions such as sodium and/or non-ionic surfactants such as tween, pluronics or PEG.

The polymer-drug combinations of this invention may be prepared for storage under conditions suitable for the preservation of drug activity as well as maintaining the integrity of the polymers, and are typically suitable for storage at ambient or refrigerated temperatures. The porous polymer scaffolds to be used for tissue engineering and tissue guided regeneration must also be sterile. Sterility may be readily accomplished by conventional methods such as irradiation or treatment with gases or heat.

The following non-limiting examples set forth hereinbelow illustrate certain aspects of the invention. All parts and percentages are by weight unless otherwise noted and all temperatures are in degrees Celsius. Dicarboxylic acids and all other reagents were purchased in pure form and were used as received. Solvents were of "HPLC grade." All diphenolic monomers (e.g., the esters of desamino tyrosil-tyrosine) were prepared according to the procedure provided in Example I of U.S. Pat. No. 5,099,060. Although this procedure refers specifically to DTH, monomers having esters other than the hexyl ester can be readily prepared by the same basic procedure. The DPTS catalyst was prepared as described by Moore, et al., *Macromol.*, 23 (1), 65-70 (1990).

EXAMPLES

The following table defines the abbreviations adopted for the diphenols, poly(alkylene oxide) dicarboxylic acids and polyarylates illustrated by the examples below:

TABLE I

| | |
|---|---|
| Desaminotyrosyl-tyrosine ethyl ester | DTE |
| Desaminotyrosyl-tyrosine hexyl ester | DTH |
| Desaminotyrosyl-tyrosine octyl ester | DTO |
| Desaminotyrosyl-tyrosine dodecyl ester | DTD |
| Poly(ethylene glycol)-1000-succinate | PEG-1K-suc |
| Poly(DTE-PEG-1000) | DTE-PEG-1000-suc |
| Poly(ethylene glycol) 600 | PEG-600 |
| Poly(DTE-PEG-600) | DTE-PEG-600 |
| Poly(ethylene glycol)-400-succinate | PEG-400-suc |
| Poly(DTE-PEG-400-suc) | DTE-PEG-400-suc |

Example 1

Preparation of DTE-PEG-1000-suc 2.644 g (0.0074 mols) of DTE and 0.653 g (0.0022 mols) of DPTS were weighed into a 125 mL round-bottom flask containing an egg-shaped magnetic stirring bar. 8.927 g of PEG-1000-succinate was weighed into a 50 mL Ehrlenmeyer flask. Using 26 mL methylene chloride, the PEG compound was transferred quantitatively to the round-bottom flask. The mixture was stirred until a pale yellow solution was obtained. 3.59 mL DIPC was added with stirring. The reaction mixture heated up and started to boil. Within 20 to 30 minutes, the solution became very viscous and stirring stopped. The reaction was stirred overnight.

The polymer solution was added to 800 mL of isopropyl alcohol (IPA) with stirring. The polymer precipitated and collected as a ball. After decanting the IPA solution, the polymer was shredded by hand and washed with IPA. The polymer was dissolved in methylene chloride and washed with water in a separatory funnel. The polymer was isolated from the methylene chloride solution by precipitation into IPA. The IPA precipitate was further washed with two portions of ether and then dried under high vacuum for 48 hours. Eight grams of a rubbery material with a weight-average molecular weight of 39,000 daltons was obtained.

Example 2

Preparation of DTE-PEG-600

Example 1 was repeated, substituting carboxymethyl PEG-600 for PEG-1000-succinate.

Example 3

Composites of PEG-polyarylates with Calcium Sulfate

The polyarylate of Example 1 was mixed thoroughly with calcium sulfate particles (particle size 10-20 mesh) with a stainless steel spatula. The wt. % of calcium sulfate was varied from 10 to 95%. Approximately 2 g of polyarylate was mixed with each of the various weight percentages of solid calcium sulfate. The observations are summarized in Table II:.

TABLE II

Composites of DTE-PEG1K-suc with calcium sulfate (particle size 10-20 mesh)

| Wt. % Calcium sulfate | Observation |
| --- | --- |
| 10 | The polymer flows and tacky |
| 25 | The polymer flows and tacky |
| 50 | Polymer flows slower along with solid particles. |
| 75 | Polymer flows relatively slower (than 50% composite) along with solid. Solid (calcium sulfate particles) and polymer settle at beaker bottom overnight |
| 90 | Composite can be shaped by hand; polymer doesn't flow |
| 95 | Composite can be shaped by hand; polymer doesn't flow |

Example 4

Drug Release Studies Using Injectable Polyarylates

Initial protein release studies were conducted using bovine serum albumen (BSA) as the model protein. While BSA has no known therapeutic value, it was selected for several reasons. First, there is a large volume of literature which allows a measure of success. Second, unlike therapeutic proteins and polypeptides, it is commercially available and inexpensive. Third, it is very stable. Finally, reliable analytical methods are available.

BSA was obtained from SIGMA (Cat # A 7906, Lot # 29H1282, Fraction V). A buffer solution, 0.1M, pH 7.4 PBS was prepared by diluting PBS powder obtained from SIGMA (CAT # P3813) per directions supplied.

Acetonitrile (HPLC grade) was obtained from FISHER (Cat #A998-4) Deionized water was collected from a BARNSTEAD Still. TFA was obtained from ACROS A HPLC method was developed for assaying BSA. The column used for BSA analysis was purchased from Phenomenex (Torrance, Calif.) with the following specifications—Jupitor Stainless steel 250×4.60 mm, Silica C4 fictionalized, 5-micron particle size, 300 A pore size. BSA was assayed by UV at 220 nm. The HPLC system used was a Perkin Elmer, equipped with a pump, UV detector and a Series 200 Auto sampler. Data was analyzed using TURBOCHROM Version 6.0 Software.

Details of the BPLC method are summarized in Table III:

TABLE III

| Step | Time, | % Water (Distilled Deionized) (TFA 0.1%) | % Acetonitrile (TFA 0.08%) |
| --- | --- | --- | --- |
| 0 | 5 | 90 | 10 |
| 1 | 1 | 60 | 40 |
| 2 | 3 | 48 | 52 |
| 3 | 10 | 48 | 52 |
| 4 | 3 | 90 | 10 |

Under these conditions, BSA elutes as a sharp peak with a retention time around 9.2 minutes (9.03 to 9.35). A calibration curve was constructed by sequential dilution of a 250 mg/25 mL (10 mg/ml) stock solution of BSA in PBS. The concentration range was 0.4 mg/mL to 40-mg/mL. The curve was found to be linear in this range, with a correlation coefficient of 0.9918.

The robustness of BSA analysis was confirmed by checking the reproducibility of multiple injections. Two BSA samples (corresponding to the highest and lowest concentrations in the standard plot) were prepared by dilution of a stock solution of BSA in PBS (BSA 0.2565 g in 25 ml PBS) and injected 3 times in the HPLC. The retention times and Area (UV*sec) were found to be reproducible with a variation of approximately 5%. The detection limit for BSA under the methodology currently used was found to be 0.5 g/20 L. (0.025 mg/mL). A very small peak that cannot be quantitated was obtained at this concentration.

The quantification limit was determined by injecting sequentially diluted samples and estimating the amount of BSA. The results were then confirmed in a blinded study. The limit was defined as the concentration at which BSA could be determined with an accuracy of ±10%. This is a relatively large margin, which is acceptable for the initial screening study, which will be narrowed during the development stage. The quantification limit was established to be 1 mg/mL. Three concentrations of BSA in PBS (n=3 for each) were provided blinded and the assay performed. The operator was able to accurately identify and quantify the samples within an error of around 10%. The standard deviation was very low (<0.2 for all sets), suggesting very good accuracy. The peak retention times were between 9.09 and 9.12 minutes for all the unknown samples, suggesting good reproducibility in terms of peak retention time. The peaks in all cases were a little asymmetric (distorted or broad on right side). The analysis was more accurate in the lower concentration ranges. This was expected since the deviation from the calibration curve is larger at the higher concentrations.

Preparation of DTE-PEG-400-suc

Example 1 was repeated, substituting PEG-400-suc for PEG-1000-succinate.

Formulation Methods

Standard Method. 500 mg of polymer is transferred into a 20 mL scintillation vial. 100 mg of BSA powder is added and stirred with a spatula until a homogeneous dispersion is obtained (about one minute, depending on polymer viscosity).

Formulation—Water Based. 500 mg of polymer is transferred into a 20 mL scintillation vial. An appropriate amount of water is added (0.5 to 2 mL) and stir with a spatula until a homogeneous dispersion is obtained (again about one minute for low viscosity polymers). If the polymer MW is high, it may be necessary to place the mixture at overnight at 37° C. 100 mg of BSA powder is added to the homogeneous dispersion and stirred until all the BSA is dissolved or dispersed.

This dispersion may be used as such or it can be freeze dried or dried under vacuum. Attempts at freeze-drying have so far resulted in phase separation of BSA from the polymer. Formulations made by this methodology have not been used in any release studies to date.

Formulation—Using Mini Max Extruder. One to two grams of polymer is placed in the extruder and the extruder temperature was set at 35° C. The polymer is stirred at maximum speed for 30 minutes. After the temperature stabilizes at 45° C. heating is stopped. 100 to 300 mg of BSA is then mixed with the polymer. When the temperature drops to 35° C. the heating is turned on again for two minutes and then switched off. The BSA-polymer mixture is then stirred for about 6 minutes. The stirrer is raised and lowered every minute. Finally the mixture is extruded into a Teflon dish. The extruded mass is a ductile, opaque yellow solid, and can be shaped by hand. The extruded mass can then be stored in a freezer.

Sample Preparation 0.1 g of BSA was dispersed in 0.5 g of polyarylate as described in the standard formulation method section. 5 mL of acetonitrile (containing 0.08% TFA) was added and the mixture was shaken overnight. To this, 45 mL of PBS was added with shaking. Polymer precipitated and a clear supernatant solution was obtained. The amount of BSA was quantified in the supernatant by HPLC as described above.

In all formulations where BSA was directly mixed into the polymer, no separate estimation of BSA was made and the loading was assumed to be the same as the amount weighed. For two the melt-extruded formulations, BSA was estimated using the method described above. The extrusion process gives uniform distribution of BSA within the polymer matrix (error <5%).

Release Study 15 mL of PBS was added to the polymer-BSA formulation prepared as described above. The vial was capped tightly and place in a 37° C. incubator shaker (rpm=200). At periodic intervals, 10 mL buffer was removed for analysis and replaced with 10 mL fresh buffer. For each formulation, three replicates were used. The amount released was reported as the average of the three replications. The BSA released was quantified using the HPLC method described above.

The sampling intervals were 1 h, 3 h, 6 h, 12 h. 24 h, and 48 h. After 24 h, the sampling interval can be reduced to once every 24 h or less depending on the rate of release.

BSA Release from DTR-PEG 600 Polymers

The release of BSA from DTR-PEG-600 ($R_2$=various desaminotyrosyl-tyrosine esters) injectable polyarylates was investigated. The aim of this study was to investigate whether BSA can be released from these polymers and to study the effect of pendant chain on the release rates. The three polymers used in this study had $R_2$=ethyl, hexyl and octyl pendant chains. The loading was 16.6%. Results that are averages of n=3 are shown in FIG. 1.

BSA was released from all polymers by a diffusion type process. The fastest release was from the most hydrophilic polymer, DTE PEG 600, where the release was completed within 18 hours. The DTH polymer gave the slowest release, which was complete within 48 hours. Interestingly, the release from the polymer with the most hydrophobic DTR moiety (DTO) was almost identical to that from the polymer with the most hydrophilic moiety (DTE), and faster than the one with intermediate hydrophobicity (DTH). It is possible that the polymer properties are dominated by the properties of PEG, which masks the influence of the pendant groups.

BSA Release from DTR-PEG 1000-Suc

Figure 2:
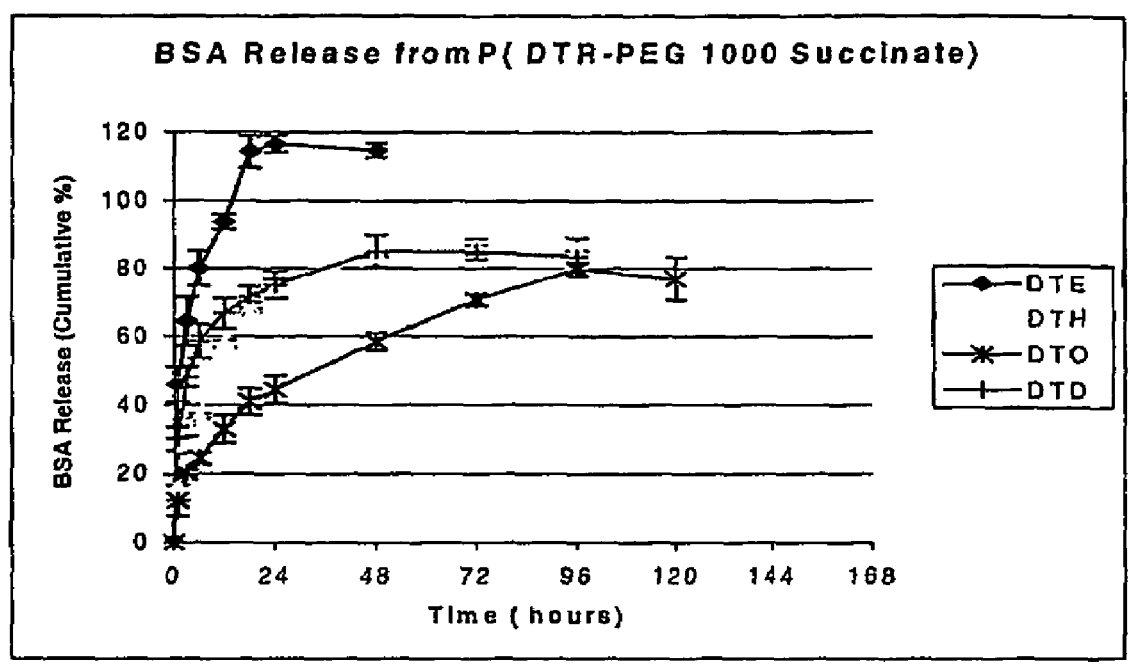
FIG. 2 depicts BSA Release from DTR-PEG-1000 Succinates (LMW)

Effect of DTR side Chain. These polymers differed structurally from the DTR PEG 600 polymers in that the PEG units are linked to the DTR units via a succinic acid unit, whereas in the DTE PEG 600 polymers the DTR and PEG units are directly linked. Four polymers, containing DTE, DTH, DTO and DTD were used. The polymers were designed to have low Molecular weights (<15,000 KD) so that they could be formulated for injection, without added excipients or heating. The loading was 16.7% and the release studies were conducted as described previously. The release curves are shown in FIG. 2.

All polymers released BSA in a diffusion type process. The rate of release was related to the nature of the side chain on the DTR monomer, in the case of the DTE, DTH and DTO polymers. The release was completed within 18 hours for the polymer with the most hydrophilic side chain (DTE) while the polymer with the most hydrophobic chain (DTO), released BSA over a period of 96 hours and the one with intermediate length (DTH) released BSA over a 48 hour period. Interestingly, the polymer with the most hydrophobic chain (DTD), (which was expected to release BSA at the slowest rate), actually released BSA faster, with the release being completed within 48 hours.

Influence of MW of PEG

DTE-PEG Suc with PEG molecular weights of 400 and 1000 were used. The polymers were rubbery materials and BSA could not be incorporated by the conventional method. The melt extrusion method was used and the loadings estimated as discussed in previous sections. The loading for the DTE PEG 400 succinate was 16.7% and for DTE-PEG 1000 Suc, it was 20%.

Figure 3:
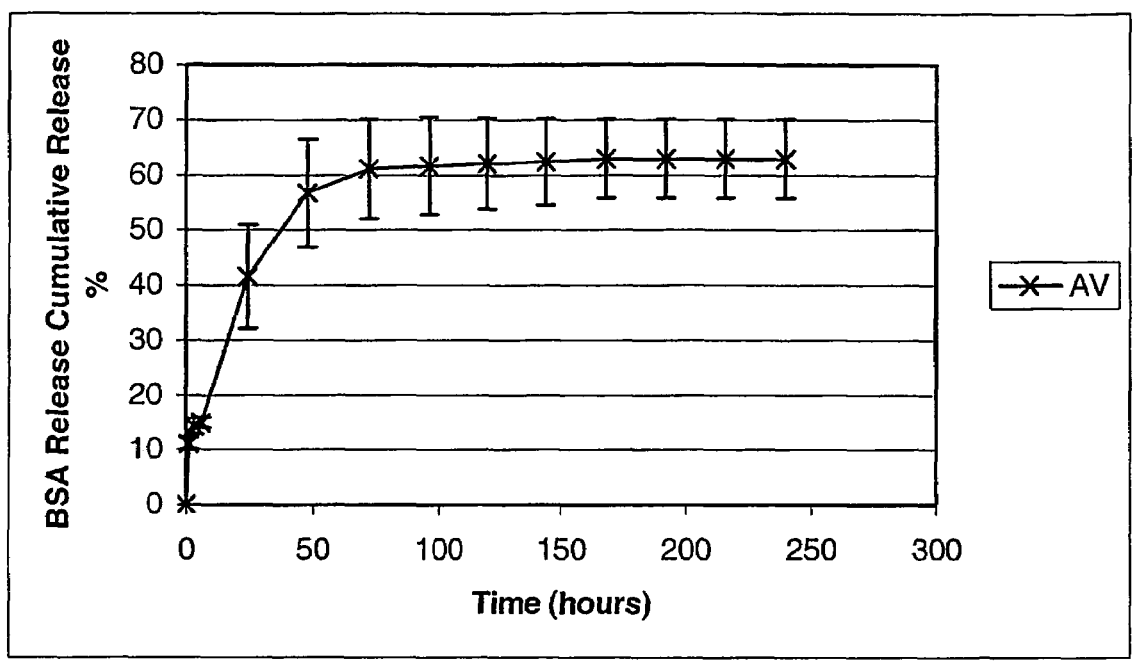
FIG. 3 depicts the effect of PEG molecular weight on BSA release from DTR-PEG 1000-Succinate.

As shown in FIG. 3, the release from the lower molecular weight PEG 400 polymer was slower than that from the PEG 1000 version. This is expected since the PEG 400 is less hydrophilic than PEG1000. 60% BSA was released in 168 hours (7 days) from the PEG 400 polymer, while 80% BSA was released in 5 days (120 hours) from the PEG 1000 polymer.

Effect of Polymer MW

Figure 4:
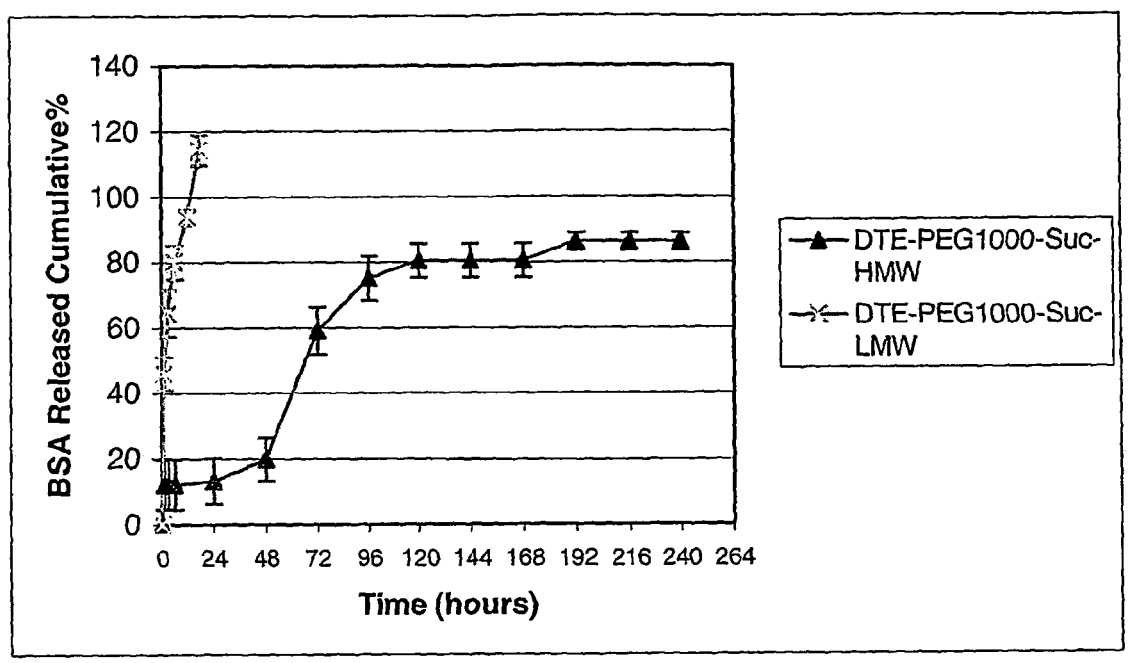
FIG. 4 depicts the effect of polymer molecular weight on BSA release from DTR-PEG 1000-Succinate.

DTE-PEG 1000-Suc with MW 35,000 and 12,000 was used (FIG. 4). The molecular weight of the polymer had a very significant effect on the release of BSA. While the release of BSA was complete in less than 1 day with the LMW polymer, only 80% was released after 5 days with the HMW polymer and the release continued for beyond 2 weeks, although at a very slow rate.

Effect of Changing the PEG Structure: DTR-PLURONIC-Suc

Figure 5:
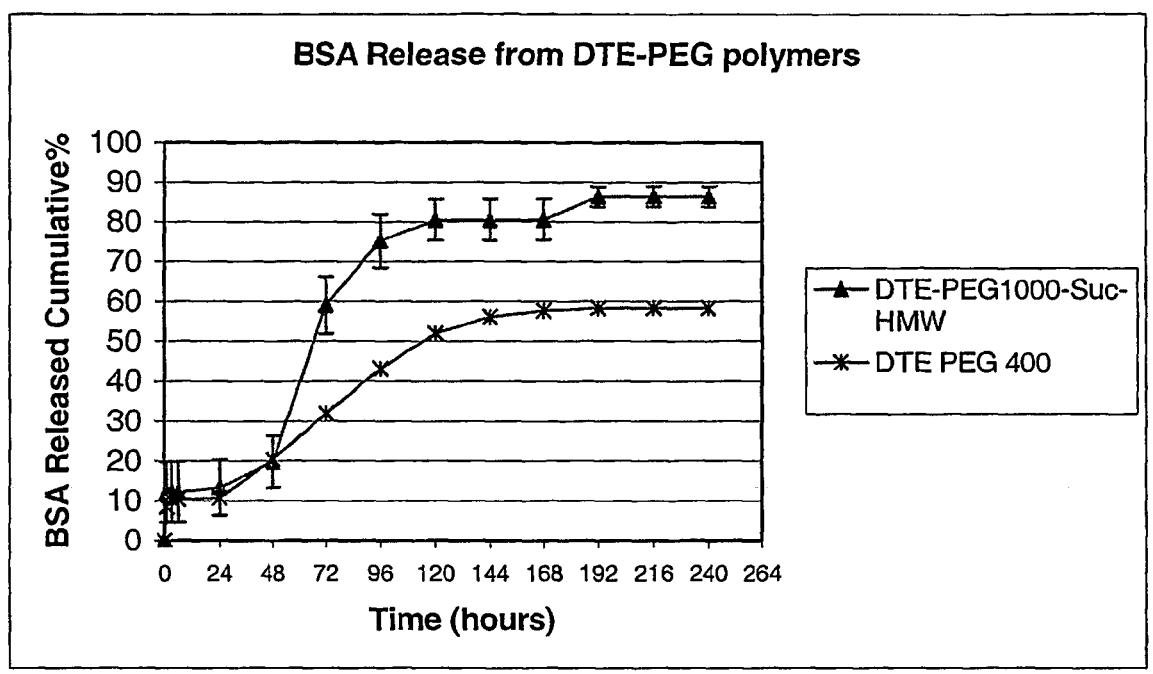
FIG. 5 depicts the effect of poly(alkylene oxide) structure on BSA release from DTR-PEG 1000 Succinate polymers.

In this family of polyarylate, the PEG unit is replaced with a more hydrophobic PLURONIC unit. DTE-PLURONIC-suc was synthesized as a typical representative of this family. BSA was incorporated into this material at 16.7% loading by direct mixing and release studies initiated as before. The release curve obtained is shown in FIG. 5. After an initial burst of 10%, an additional 45% is released within 48 hours, after which the release seems to stop. A review of the BPLC traces showed that the BSA peak is broad and asymmetrical.

Polyarylate Degradation

The degradation of the polyarylates was monitored by GPC. (THF, polystyrene standards). Since the release rates are completed within short periods of time, the MW was measured at time zero, after completion of release (about 1 week) and then at weekly intervals until the polymer is fully resorbed. The data for the are presented in the following two tables (Tables IV and V).

TABLE IV

Degradation of DTR-PEG600) ® = E, H, O) polymers

| Polymer | Initial (N = 1) ($M_w$) | After Day 7 (N = 3) ($M_w$) | After Day 14 (N = 3) ($M_w$) |
|---|---|---|---|
| DTE PEG 600 | 12300 | 8200(Shows another low MW peak and shoulder) | 4200 (Clearly shows two peaks. (One low mol. wt peak) |
| DTH PEG600 | 12600 | | 2700 (Clearly shows two peaks. (One low mol. wt peak) |
| DTO PEG600 | 6800 | | 2900 (Clearly shows two peaks. (One low mol. wt peak) |

TABLE V

Degradation of DTR-PEG1000-Suc ® = E, H, O, D)

| Polymer | Before ($M_w$) | After Day 7 ($M_w$) | After Day 14 ($M_w$) |
|---|---|---|---|
| DTE-PEG 1000-Suc/LMW* | 16900 | 14700 | 13600 |
| DTH-PEG 1000-Suc/LMW* | 18800 | 16400 | 14600 |
| DTO-PEG 1000-Suc/LMW* | 20050 | 15800 | 13800 |
| DTD-PEG 1000-Suc/LMW* | 16300 | 16300 | 14600 |

The polyarylates made from the PEG dicarboxylic acid degrade at a faster rate than those made from PEG-Succinates. It is expected that these all polymers will break down to monomeric units within 4 to 6 weeks. This is of significance since it will allow for repeated dosing of the same patient without accumulation of polymer.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

What is claimed is:

1. A polyarylate comprising repeating units having the structure:

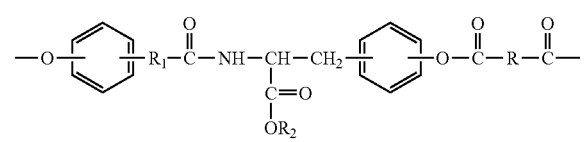

wherein $R_1$ is CH=CH or $(CH_2)_n$ wherein n is from 0 to 18, inclusive; $R_2$ is selected from the group consisting of hydrogen and straight and branched alkyl and alkylaryl groups containing up to 18 carbon atoms; and R has the structure:

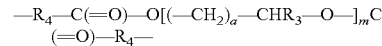

wherein a is from 1 to 3, inclusive, m is from 1 to 500,000, inclusive, $R_3$ is hydrogen or a lower alkyl group containing from one to four carbon atoms, and $R_4$ is selected from the group consisting of a bond and straight and branched alkyl and alkylaryl groups containing up to 18 carbon atoms.

2. The polyarylate of claim 1, wherein $R_1$ is —$CH_2$—$CH_2$—.

3. The polyarylate of claim 1, wherein $R_2$ is selected from the group consisting of ethyl, butyl, hexyl, octyl and benzyl groups.

4. The polyarylate of claim 1, wherein a is 1, $R_3$ is hydrogen and m is between about 10 and about 100.

5. The polyarylate of claim 1, wherein $R_4$ contains up to 12 carbon atoms.

6. The polyarylate of claim 5, wherein $R_4$ is selected from the group consisting of —$CH_2$—$CH_2$—C(=O)—, —CH=CH—, —$CH_2$—CH(—OH)—, —$CH_2$—C(=O)— and (—$CH_2$—$)_z$, wherein z is between 0 and 12, inclusive.

7. The polyarylate of claim 1, in combination with hydroxyapatite, calcium sulfate, tricalcium phosphate, demineralized bone matrix or bioglass.

8. An implantable medical device comprising the polyarylate of claim 1.

9. The implantable medical device of claim 8, wherein said device is a stent, film or polymeric scaffold for tissue engineering.

10. The implantable medical device of claim 8, wherein the surface of said device is coated with said polyarylate.

11. The implantable medical device of claim 10, wherein said device is a stent, film or polymeric scaffold for tissue engineering.

12. The implantable medical device of claim 8, comprising a biologically or pharmaceutically active compound in combination with said polyarylate, wherein said active compound is present in an amount sufficient for therapeutically effective site-specific or systemic drug delivery.

13. The implantable medical device of claim 12, wherein said active compound is a pharmacologically active protein, peptide, vaccine or gene.

14. The implantable medical device of claim 12, wherein said active compound is covalently bonded to said polyarylate.

15. A controlled drug delivery system comprising a biologically or pharmaceutically active compound in combination with the polyarylate of claim 1, wherein said active compound is present in an amount sufficient for therapeutically effective site-specific or systemic drug delivery.

16. The controlled drug delivery system of claim 15, wherein said active compound is physically coated with said polyarylate.

17. The controlled drug delivery system of claim 15, wherein said active compound is physically admixed with or covalently bonded to said polyarylate.

18. The controlled drug delivery system of claim 15, wherein said active compound is embedded or dispersed in said polyarylate.

19. The controlled drug delivery system of claim 15, wherein said active compound is a pharmacologically active protein, peptide, vaccine or gene.

20. The controlled drug delivery system of claim 15, comprising micro-particles loaded with said active compound suspended in a matrix of said polyarylate.

21. The controlled drug delivery system of claim 20, wherein said active compound is a pharmacologically active protein, peptide, vaccine or gene.

22. A method for site-specific or systemic drug delivery comprising implanting in the body of a patient in need thereof the implantable medical device of claim 12, 13 or 14.

23. A method for site-specific or systemic drug delivery comprising administering to a patient in need thereof the drug delivery system claim 15, 16, 17, 18, 19, 20 or 21.

24. An implantable medical device in the form of a sheet for use as a barrier for surgical adhesion prevention consisting essentially of the polyarylate of claim 1.

25. A method for preventing the formation of adhesions between injured tissues comprising inserting as a barrier between said injured tissues the sheet of claim 24.

26. An injectable drug delivery system consisting of the polyarylate of claim 1 and a biologically or pharmaceutically active compound in an amount sufficient for therapeutically effective site-specific or systemic drug delivery.

27. The injectable drug delivery system of claim 26, wherein said active compound is a pharmacologically active protein, peptide, vaccine or gene.

28. The injectable drug delivery system of claim 26 or 27, wherein microparticles containing said active compound are suspended in said polyarylate.

29. The injectable drug delivery system of claim 26 or 27, wherein said system is excipient-free.

30. A method of forming an excipient-free injectable drug delivery system com-prising directly mixing the polyarylate of claim 1 and a biologically or pharmaceutically active compound in an amount sufficient for therapeutically effective site-specific or systemic drug delivery.

31. The method of claim 30, wherein microparticles comprising said active compound are mixed with said polyarylate.

32. The method of claim 30 or 31, wherein said active compound is a pharmacologically active protein, peptide, vaccine or gene.

33. In a surgical method for repairing diseased or damaged bone tissue comprising applying to said tissue a putty-like substance, the improvement comprising said putty-like substance comprising the polyarylate of claim 1 or 7.

34. In a cosmetic reconstructive surgery method comprising applying a filler material to soft tissues, the improvement comprising said filler material consisting essentially of the polyarylate of claim 1.

35. The method of claim 34, wherein said filler material consists of said polyarylate.

36. The method of claim 34 or 35, wherein said polyarylate is radio-opaque.

37. A method of regulating cellular attachment, migration and proliferation on a polymeric substrate, comprising contacting living cells, tissues or biological fluids containing living cells with the polyarylate of claim 1.

38. The method of claim 37, wherein said polyarylate is in the form of a coating on the surface of a medical implant.

39. The method of claim 37, wherein said polyarylate is in the form of a film.

40. The method of claim 37 wherein said polyarylate is in the form of a polymeric tissue scaffold.

41. The method of claim 33, wherein said polyarylate is radio-opaque.

42. The polyarylate of claim 1, wherein m is between about 10 and about 100.

43. The polyarylate of claim 42, wherein m is between about 10 and about 50.

\* \* \* \* \*